(12) United States Patent
Makkee et al.

(10) Patent No.: US 8,440,845 B2
(45) Date of Patent: May 14, 2013

(54) PROCESS FOR CONVERTING POLYSACCHARIDES IN AN INORGANIC MOLTEN SALT HYDRATE

(75) Inventors: Michiel Makkee, Delft (NL); Jacob Adriaan Moulijn, The Hague (NL); Rafael Menegassi De Almeida, Rio de Janeiro (BR); Paul O'Connor, Hoevelaken (NL)

(73) Assignee: BIOeCON International Holding N.V., Curaçao ( * ) Notice: Subject to any disclaimer, the term of this patent is extended or adjusted under 35 U.S.C. 154(b) by 33 days.

(21) Appl. No.: 13/235,575

(22) Filed: Sep. 19, 2011

(65) Prior Publication Data

US 2012/0108827 A1    May 3, 2012

Related U.S. Application Data (63) Continuation of application No. PCT/EP2010/053359, filed on Mar. 16, 2010.

(60) Provisional application No. 61/160,769, filed on Mar. 17, 2009.

(51) Int. Cl.
C07D 493/04    (2006.01)
C07D 307/20    (2006.01)

(52) U.S. Cl.
USPC .......................................... 549/464; 549/476

(58) Field of Classification Search .................. 549/464, 549/476
See application file for complete search history.

(56) References Cited

U.S. PATENT DOCUMENTS

| | | |
|---|---|---|
| 257,607 A | 5/1882 | Parkes |
| 607,091 A | 7/1898 | Simonsen |
| 647,805 A | 4/1900 | Classen |
| 4,018,620 A | 4/1977 | Penque |
| 4,313,884 A | 2/1982 | Arena |
| 4,452,640 A | 6/1984 | Chen et al. |
| 6,013,812 A | 1/2000 | Haas et al. |
| 6,407,266 B2 | 6/2002 | Bhatia |
| 6,689,892 B2 | 2/2004 | Andrews et al. |
| 6,831,181 B2 | 12/2004 | Bhatia |
| 6,864,378 B2 | 3/2005 | Bhatia |
| 2007/0173651 A1 | 7/2007 | Holladay et al. |
| 2007/0173652 A1 | 7/2007 | Holladay et al. |
| 2007/0173653 A1 | 7/2007 | Hu et al. |
| 2007/0173654 A1 | 7/2007 | Holladay et al. |
| 2007/0282042 A1 | 12/2007 | East |

FOREIGN PATENT DOCUMENTS

| | | |
|---|---|---|
| EP | 0091221 A2 | 10/1983 |
| EP | 2011569 A1 | 1/2009 |
| WO | 00/14081 A1 | 3/2000 |

OTHER PUBLICATIONS

Steffen Fischer et al: "Evaluation of molten inorganic salt hydrates as reaction medium for the derivatization of cellulose" Cellulose, Kluwer Academic Publishers, vol. 9, No. 3-4,Sep. 1, 2002 , pp. 293-300.
Werpy, T. et al. Top value added chemicals from biomass. vol. I: Results of screening for potential candidates from sugars and synthesis gas. USA DOE (Department of Energy) Report, 2004.
Heinze, T. et al. Unconventional methods in cellulose functionalization, Progress in Polymer Science 26 (9) (2001) 1689-1762.
El Seoud, et al. Organic esters of cellulose: New perspectives for old polymers. Advances in Polymer Science, vol. 186, (2005), p. 103-149.
Lehmann, C. G. Physiological Chemistry, vol. I, Blanchard & Lea, Philadelphia,1855, p. 267.
N. J. Cao, et al. Acid-hydrolysis of cellulose in zinc-chloride solution, Applied Biochemistry and Biotechnology 51-2 (1995) 21-28.
P. L. Ragg et al, The development of a process for the hydrolysis of lignocellulosic waste, Philosophical Transactions of the Royal Society of London Series A—Mathematical Physical and Engineering Sciences 321 (1561) (1987) 537-547.
Flèche, G. et al. Isosorbide—preparation, properties and chemistry. Starch / Stärke, vol. 38, n 1, (1986), S 26-30.
Stoss, P.; Hemmer, R., 1,4:3,6-dianhydrohexytols. Advances in Carbohydrate Chemistry and Biochemistry, vol. 49 (1991), p. 93-173.
Bock, K. et al, Acid catalyzed dehydration of alditols. Part I—D-glucitol and D-mannitol. Acta Chemica Scandinavica B, vol. 35 (1981), p. 441-449.
Montassier, C. et al. Deactivation of supported copper based catalysts during polyol conversion in aqueous phase. Applied Catalysis A: General, vol. 121 (1995), p. 231-244.
Montassier, C. et al. Polyol conversion into furanic derivatives on bimetallic catalysts; nature of the catalytic sites. Journal of Molecular Catalysis, vol. 91 (1994), p. 119-128.
Montassier, C. et al. Preparation and characterization of copper based bimetallic catalysts. Journal of Molecular Catalysis, vol. 91 (1994), p. 107-117.
Duclos, A. et al. A simple conversion of polyols into anhydroalditols. Synthesis, Oct. 1994, p. 1087-1090.
ISR and Written Opinion from PCT/EP2010/53359 issued by the EPO, (2010).

*Primary Examiner* — Bernard Dentz
(74) *Attorney, Agent, or Firm* — Coraline J. Haitjema; David P. Owen; Hoyng Monegier LLP (57) ABSTRACT

A process is disclosed for converting a polysaccharide-containing biomass material to platform chemicals.
The process comprises dissolving the polysaccharides in an inorganic molten salt hydrate, converting the polysaccharides to monosaccharides, and converting the monosaccharides to derivatized (di)anhydro sugars that are easily separable from the inorganic molten salt hydrate.
The derivatized (di)anhydro sugars are useful as fuel additives and fuel substitutes.

33 Claims, 4 Drawing Sheets

PROCESS FOR CONVERTING POLYSACCHARIDES IN AN INORGANIC MOLTEN SALT HYDRATE

CROSS REFERENCE TO RELATED APPLICATIONS

This application is a continuation of PCT application number PCT/EP2010/53359, filed on 16 Mar. 2010, which claims priority from U.S. provisional patent application 61/160,769 filed on 17 Mar. 2009. Both applications are hereby incorporated by reference in their entireties.

BACKGROUND OF THE INVENTION

1. Field of the Invention

The present invention relates to a process for converting polysaccharides, in particular lignocellulosic biomass material, in an inorganic molten salt hydrate to platform chemicals. The invention relates further to polysaccharide conversion products that are poorly soluble in the inorganic molten salt hydrate, and are suitable for use as fuel additives and/or fuel substitutes.

2. Description of the Related Art

In view of environmental concerns, there is a need for platform chemicals from renewable resources. The term platform chemicals is used to describe chemicals that are versatile starting materials for making specialty chemicals, and include sorbitol (or glucitol, alcohol sugar of glucose), xylitol/arabinitol (sugar alcohols from xylose and arabinose) and isosorbide (dianhydro-D-glucitol) and anhydrosugars [1].

It is considered a technical barrier to obtain (di)anhydro sugars production by selective dehydration of polyols, without side reactions. To produce such polyol dehydration products it is necessary to produce sugars, and subsequently hydrogenate such sugars to polyols. Several ways for producing sugars from lignocellulosic material are known in the art, and several ways for producing polyols from sugar are known in the art. A known method for producing sugars from cellulosic material is by acid hydrolysis.

U.S. Pat. No. 647,805 and U.S. Pat. No. 607,091 describe such hydrolysis processes, the first being a concentrated acid hydrolysis and the second a diluted acid hydrolysis. On the one hand, the diluted acid hydrolysis processes have a low yield, but do not need much further processing (acid removal) to separate and use the glucose formed. On the other hand, concentrated acid processes have higher yields but present difficulties in sugar recovery/acid separation. Processes for acid neutralization and removal, concentration of syrup and precipitation of sugars are known to those skilled in the art.

The fact that certain compounds are capable of dissolving cellulose is used in the art to derivatize cellulose to other chemicals. Heinze and coworkers [2], [3] provide an overview of the technology of dissolution of cellulose for derivatization.

Polysaccharides, such as cellulose, lignin and starch are easily dissolved in certain concentrated metal halides, like zinc halides ([4] and U.S. Pat. No. 257,607. Similarly, processes were developed to provide a faster, higher yield for cellulose hydrolysis to glucose, based on the concept of dissolution of the cellulose and further hydrolysis of cellulose to glucose in homogeneous media.

Calcium chloride concentrated solutions (5 to 55 wt %) with small amount of HCl (from 0.01% to 2 wt %) were used to hydrolyze cellulose to monosaccharides, U.S. Pat. No. 4,018,620. The calcium chloride was partially separated from the remaining solution by crystallization, but further removal of ions $Ca^{2+}$ and $Cl^-$ were necessary. The swelling effect of the salt is believed to enhance the hydrolysis.

U.S. Pat. No. 4,452,640 discloses a process to dissolve and quantitatively hydrolyze cellulose to glucose without formation of degradation products, using $ZnCl_2$ solutions. Dissolution was effected with salt solutions, with 60 to 80 wt % $ZnCl_2$ being preferred, at sufficiently large contact time and temperatures of 70 to 180° C., preferably 100 to 145° C. After dissolution, it was claimed that lowering the $ZnCl_2$ concentration (to 40 to 50 wt %) was further necessary prior to hydrolysis, to avoid glucose degradation, and subsequently HCl or a similar dilute acid was added to effect hydrolysis (down to pH<2).

A later publication of the same group showed results without the salt concentration lowering step [5]: experiments with dissolution media comprising 67 wt % of $ZnCl_2$ were performed at temperatures of 50 to 100° C. and 2 hours time. Additional acid showed to be necessary to effect hydrolysis, 0.5 mol/L of solution being the optimum, with low conversion at lower concentrations and low yield at higher concentrations.

A reasonable temperature was 70° C., hydrolysis being incomplete at lower temperatures, and further conversion of glucose to other products at 100° C. Experimental ratios of $ZnCl_2$ to cellulose were from 1.5 to 18. The higher the $ZnCl_2$/cellulose ratio the higher was the yield of glucose. Contrary to previous teaching (U.S. Pat. No. 4,452,640), the presence of $ZnCl_2$ lowered the degradation of glucose, in comparison to an aqueous solution of the same HCl content. Concentrated salt solutions were preferred, as solutions with increased water content were unable to dissolve cellulose, thus affecting the hydrolysis rate.

European Patent Application EP 0 091 221 A teaches the hydrolysis of cellulose or starch in solubilization media comprising water, an inorganic acid and hydrated halide of aluminum, optionally containing and additional metal halide, with yields close to 100%. Longer hydrolysis times than the necessary lead to a lower yield of glucose due to degradation.

Ragg and Fields from Imperial Chemical Industries (ICI) teach a process for hydrolysis of lignocellulosic waste using metal halides and hydrochloric acid as catalysts [6].

Several salts where tested to effect hydrolysis, LiCl and $CaCl_2$ solutions were considered the most effective, $ZnCl_2$, $MgCl_2$ and $CaCl_2$ being somewhat less effective, and $FeCl_3$, $SnCl_4$, NaCl, KCl, $MnCl_2$, $NiCl_2$, $CuCl_2$, $CoCl_2$ and $CdCl_2$ being the least effective. Typical conditions were 60-90° C., 15 to 25 wt % of cellulose substrate, in a dissolution medium containing 5-40 wt % of $CaCl_2$ and 25-40 wt % of HCl, pressure of 4-7 bar to maintain a liquid phase, and reaction times of 10 to 20 minutes, yielding more than 85 wt % of glucose.

Another advantage of the salts is the breaking of the azeotrope formed by HCl and water in reaction media with more than 15 wt % of $CaCl_2$—making it easier to separate the HCl from the solution, which can be done with a simple evaporator.

Glucose, the desired product of processes of cellulose hydrolysis, needs to be further separated from the concentrated salt media in such processes. Besides precipitation of part of the salt ($CaCl_2$ concentrated solutions, U.S. Pat. No. 4,018,620), ion exchange and chromatographic methods (U.S. Pat. No. 4,452,640 and [5]) or even electrodialysis [6] were considered.

In all these separation procedures, the salt—the main compound of the solution—is to be removed, which increases the separation cost. Other usual separation procedures such as vaporization cannot be used as glucose degrades at higher temperatures. Extraction is not an option, as both the salt and glucose are soluble in water.

A desired product of glucose is sorbitol, a hydrogenation product of glucose. A further desired product of sorbitol is the dianhydro sorbitol, or isosorbide, which is a product of double dehydration of sorbitol.

Reviews of Flèche [7] and Stoss [8] present the uses, properties and chemistry of isosorbide, the disclosures of which are incorporated herein by reference.

Methods for producing isosorbide involve the dehydration of sorbitol (D-glucitol) in acidic solutions. Protonation due to the presence of acid occurs preferentially at the primary glucitol hydroxyl group. The first internal dehydration step leads to 1-4 anhydro-D-glucitol. The dehydration can also take place at the 3 and 6 positions, leading to the 3,6-anhydro isomer [9]. Further dehydration of both isomers leads to the 1,4-3,6 dianhydro-D-glucitol, or isosorbide. Another possible first dehydration occurs at the 1,5 and 2,5 positions. In these positions no second intramolecular dehydration is observed, yielding the monoanhydride derivative. Another complicating problem is the possibility of intramolecular elimination of water between two molecules, leading to higher molecular oligomeric or polymeric units.

The teachings of most prior art patents deal with attempts of increasing the selectivity by preventing the formation of polymeric units and working in conditions where 1,5 and 2,5 dehydration products are less favored.

Acidic catalysts mainly used in the dehydration of sorbitol are $H_2SO_4$, phosphoric acid, HCl and other acids such as p-toluene sulfonic, methanesulfonic acid. Solid catalysts can be used such as acidic ion exchange resins, zeolites, and sulfated zirconia.

According to the state of the art of dehydration using acidic catalysts, dehydration conditions should be as anhydrous as possible. To accomplish this, dehydration is effected under vacuum (WO 00/14081), or with a flux of inert gas to effect water removal (for instance, using nitrogen, as taught by U.S. Pat. Nos. 6,407,266 and 6,689,892). Temperature limits are 170° C. in the presence of acid—above that significant char and tarring are to be expected, as U.S. Pat. No. 6,831,181 teaches.

It is possible to separate the isosorbide from the reaction mass using vacuum, as it has a vapor pressure of 2 mm Hg at 140° C.-145° C. and the vapor pressure of anhydroglucitol is just 0.04 mmHg at the same temperature. Process schemes involving separation and reaction using acidic catalysts are known in literature. U.S. Pat. No. 6,831,181 teaches such a process.

Besides the 1,5 and 2,5 monoanhydrohexitols, the formation of oligomeric and polymeric anhydrides is a problem—so, process schemes have been suggested whereby water is added after the reaction, to precipitate the polymers (but not dimers or monoanhydrides). In such a continuous process, a purge is necessary for removal of the non-reactive 1,5 and 2,5 monanhydrohexitols. Such procedures of recycle, precipitation and purge are taught by U.S. Pat. Nos. 6,831,181 and 6,864,378. Also, to further inhibit the formation of 2,5 monoanhydrohexitols, it is taught by US Patent Application 20070173651 to perform the reaction in acidic media in 2 temperature steps, a first step lower than 120° C., and a second step higher than 120° C. Furthermore, according to US Application 20070173652, it would be interesting to remove water from the polyol before the first dehydration, and after the first dehydration, and preferably during the first dehydration.

When using solid catalysts, such as acidic resins, to effect the dehydration, deactivation of the catalyst is a further problem. US 20070173653 teaches periodic catalyst washing with certain protic or aprotic solvents to ensure a longer catalyst life.

The literature also teaches procedures to prevent the formation of degradation oligomers and polymers involving hydrogenation under dehydration conditions, as in U.S. Pat. No. 6,013,812 and US Patent Application 20070173654.

US Patent Application 20070173654 teaches the use of a hydrogenation catalyst during dehydration of a (preferably anhydrous) sugar alcohol, in the presence of an acidic catalyst. The hydrogenation catalyst contains a metal selected from Pd, Pt, Ni, Co, Ru, Re, Rh, Ir and Fe, and a support, which is preferably carbon, or alternatively zirconia, titania, niobia, silica or tin oxide. It is also possible to employ bifunctional catalysts, combining acidic and hydrogenation functions. The pressure is lower than 35 bar, preferably less than 20 bar, or even less than 10 bar, and preferred temperatures range from 110° C. to about 170° C. The same patent teaches the possibility of using hydrogen flow in the countercurrent mode, as a way of effecting further water removal.

U.S. Pat. No. 6,013,812 teaches the use of hydrogenation and acidic catalysts in a hydrogen atmosphere to effect dehydration of polyols. Without claiming a particular catalyst, the authors used Pd/C and Ru/C and additional acids in the examples. In the presence of a catalyst, less than 1 wt % polymers, but significant amounts of low molar weight polyols were formed, products of metal catalyzed hydrogenolysis. Without acidic catalysts there is insufficient conversion of D-sorbitol. Raney Cu, Co/Cu/Mn, Raney Ni and Cr—Ni were also tested in the absence of acid, and in spite of a high conversion (hydrogenolysis) the formation of isosorbide was lower than 2 wt %.

MONTASSIER et al [10], [11], [12] teach the use of Cu/C or bimetallic copper catalysts to effect the dehydration of D-glucitol and other polyols under hydrogenation conditions, without added acids. Apparently, ionic copper compounds formed during the reaction in the catalyst surface are significantly electrophilic and capable of interacting strongly with the polyol hydroxyl groups, weakening the C—O bond, and thus catalyzing the formation of the cyclic internal dehydration products. Bimetallic copper-based catalysts, such as Cu/Ru, are also active, as the presence of Ru enhances the polarity of Cu. Unfortunately, the stability of such catalysts is extremely low (hours), due to the leaching of copper compounds. Hydrogenolysis byproducts are also formed. Stability of the catalyst could be enhanced to some extent by addition of NaCl.

U.S. Pat. No. 4,313,884 teaches that metal ions with a charge-to-ionic-radius ratio from about 2.0 to about 3.2 catalyze the dehydration of hexitols, at a temperature from about 100 to about 300° C., preferably from 150 to 250° C. A hexose, such as D-glucose, may be converted directly to anhydrohexitols by the hydrogenation in the presence of a hydrogenation catalyst to which the appropriate metal salt has been added. The metal ion-to-polyol ratio is from about 0.01 to about 0.1. Claimed salts are the ones with ions selected from the group consisting of magnesium, manganese, iron, cobalt, nickel, copper, actinium, thorium, protactinium, uranium, cerium, praseodymium, neodymium, promethium, samarium, europium, gadolinium, terbium, dysprosium, holmium, erbium, thulium, ytterbium and lutetium. In the examples the dehydration of D-glucitol is effected in a 33 wt % aqueous solution containing a metal chloride at a mole ratio of 0.05 to D-glucitol, together with a nickel hydrogenation catalyst, without additional acid, yielding hydrogenolysis products (1,2-propylene glycol, ethylene glycol, glycerin and mannitol) and monoanhydro and dianhydro-D-glucitol.

DUCLOS et al. [13] teach that heating D-glucitol in anhydrous pyridine chloride (ionic liquid) at 120 to 160° C. for several hours (above 4 h) lead to 1,4-anhydro-D-glucitol and, to a lesser extent, 1,4:3,6-dianhydro-D-glucitol. Surprisingly, the authors observed no 1, 5 or 2,5 anhydro-D-glucitols.

Prior art publications mostly consider the use of anhydrous D-glucitol as feedstock, or prefer the removal of water present prior to dehydration and also during dehydration—so there are several previous steps to prepare feedstock to dehydration and additional production of glucitol from glucose, and production of glucose from cellulose or starch or other suitable means.

In none of the publications product was formed without by-products, such as polymerization products, 2,5-anhydro-D-glucitols, hydrogenolysis products—or with full conversion to the desired isosorbide product.

So there is a need for a process that is able to produce isosorbide with enhanced yield and with reduced formation of by-products.

There is a further need for a process that converts isosorbide and similar dianhydro sugars to compounds that are poorly soluble in inorganic molten salt hydrates.

Also, there is a need for processes to convert cellulose to glucose and further derivatives, preferentially a platform chemical, with enhanced conversion, such as those obtained in cellulose hydrolysis in homogeneous media.

Unfortunately, the separation of glucose from the dissolution agents is difficult in the hydrolysis in homogeneous media.

An object of the present invention is to solve or mitigate the above problems

BRIEF SUMMARY OF THE INVENTION

Disclosed is a process for the conversion of polysaccharides to anhydro polyols with minimized formation of byproducts, comprising contacting the material with an inorganic molten salt hydrate, in a ratio molten salt hydrate to lignocellulosic material of 1 to 50 wt/wt, and subjecting the mixture to the sequential steps of:

a) Hydrolysis: contacting the polysaccharide with a molten salt hydrate composition and an inorganic soluble acid; conditions being resulting acid molality of mixture from 0.1 to 2.0 molal, temperature from 50 to 150° C. and LHSV from 0.2 to 2 h$^{-1}$.

b) Hydrogenation: contacting the molten salt hydrate composition and sugars mixture obtained in step a) with a hydrogenation catalyst and hydrogen until full conversion of sugars to polyols; conditions being temperature from 60° C. to 160° C. and pressure of 1.0 to 20 MPa and LHSV from 0.05 to 10 h$^{-1}$.

c) Dehydration: increasing the temperature of the inorganic molten salt hydrate composition and polyols mixture to effect full dehydration of polyols to dehydration products; conditions being pressure of 0.1 to 10 MPa, temperature from 160 to 320° C. and LHSV from 0.1 to 10 h$^{-1}$.

d) Recovery: separating anhydro polyols dehydration products and excess water from the hydrated inorganic molten salt composition, the hydrated inorganic molten salt after recovery step d) being directed to step a).

Said molten salt hydrate compositions are, for example, molten salt hydrates comprising at least Zn, Ca or Li halides, or mixtures thereof, with a content of 40 to 80 wt % of salt in said composition.

In a preferred embodiment an additional transition metal salt is added to the molten salt hydrate solution. The molar ratio of additional salt to polyol, prior to step c) is from 0.01 to 5. Preferred additional transition metal salts are the salts of copper or nickel, preferably $NiCl_2$ or $CuCl_2$.

Preferably at least 50% of the inorganic soluble acid is removed after hydrolysis, prior to hydrogenation.

In a preferred embodiment the process feedstock is a lignocellulosic material containing cellulose, hemicellulose and lignin, with hemicellulose being removed prior to step a) by any of the means known in the art (such as extraction with hot water), whereby the lignin is separated after the hydrolysis step a), the main product being 1,4:3,6 dianhydro-D-glucitol (isosorbide).

In a particularly preferred embodiment the feedstock comprises saccharose, such as raw saccharose from a sugar refinery; sugar cane or sugar beet residue containing residual sugar; and whole sugar cane or sugar beet biomass.

In another preferred embodiment the process feedstock is a lignocellulosic material containing cellulose, hemicellulose and lignin, wherein the lignin is separated after the first a) hydrolysis step, and the products being the products of the dehydration of C5 and C6 polyols.

In another preferred embodiment the process feedstock is cellulose, and the main product is 1,4:3,6 dianhydro-D-glucitol.

In a preferred embodiment the hydrolysis step is conducted in the absence of a mineral acid.

In another preferred embodiment the dehydration step is conducted in a molten salt medium containing substantially one inorganic cation.

In another preferred embodiment the dianhydro sugars are converted in the inorganic molten salt medium to compounds that are less soluble in the inorganic molten salt medium, and can as a result be readily separated from the medium. Examples of such further conversion reactions are esterification and etherification. The resulting products are suitable as fuel additives and/or fuel substitutes.

An important advantage of the use of an inorganic molten salt hydrate medium is the fact that the feedstock may contain significant amounts of water. By contrasts, organic Ionic Liquids require the substantial absence of water, which makes them unsuitable for unrefined feedstocks, such as agricultural products and agricultural waste materials, which generally contain significant amounts of water.

The reaction to isosorbide involves the generation of water. Inorganic molten salt hydrates maintain their solvent properties as water is produced in the reaction, whereas organic Ionic Liquids generally lose their solvent properties as water is generated in the reaction.

DESCRIPTION OF ILLUSTRATIVE EMBODIMENTS

The present invention relates to a process for the conversion of polysaccharides, such as lignocellulosic material components, to sugars, then polyols and finally to certain dehydration products, the conversion steps being effected in an inorganic molten salt hydrate medium.

More specifically, the invention relates to the conversion of cellulose and starch to sorbitol and subsequently to dehydration products. Besides cellulose, hemicellulose is also a possible feedstock. Cellulose and starch are polymers of glucose units, linked respectively by β glucosidic bonds and a bonds. Hemicelluloses are polymers of C6 sugars, including glucose, mannose, galactose, and rhamnose, and C5 sugars such as xylose, and arabinose.

A particularly desirable feedstock for the process of the invention is sugar-containing biomass material. Examples include saccharose, such as raw saccharose from a sugar refinery; sugar cane or sugar beet residue containing residual sugar; and whole sugar cane or sugar beet biomass material.

In one embodiment, hemicelluloses are previously removed from the lignocellulosic material, as the separation of hemicellulose fraction from biomass is easily effected with hot water treatment or aqueous phase diluted acid hydrolysis. Hemicelluloses can be further fermented to produce ethanol.

In another embodiment hemicellulose as may be present in the feedstock is left in the inorganic molten salt medium upon dissolution of the feedstock. The hemicellulose is then subjected to the conversion reactions of the process of the invention. In this embodiment a mixture of C6 and C5 (di)anhydro sugars is formed. Upon derivation, such as esterification or etherification, a product mixture is obtained that is readily separated from the inorganic molten salt hydrate medium, and can be used as, for example, a fuel substitute or a fuel additive.

Examples of suitable lignocellulosic materials include wood pulp, bagasse (in particular sugar cane bagasse), sawdust, cotton linter, stover, corn, straw, grasses, paper, forestry residues, sugar beet pulp, agriculture residues, algae, among others. In general any feedstock having at least 20 wt %, preferably 40 wt % of cellulose is suitable.

Lignocellulosic material is preferably pretreated to ensure a good contact with the molten salt hydrate media. Pretreatment may include comminution effected by cutting, crushing, grinding and/or rasping. Preferably, crushers are used followed by grinders. In one of the preferred embodiments, comminution of the lignocellulosic biomass material is effected in the first step, before the contact with the molten salt hydrate medium. In another preferred embodiment, the comminution is effected during the contact with the molten salt hydrate medium.

According to the invention, the water content of the mixture of the inorganic molten salt hydrate media and the ligno-cellulosic biomass material results in a total water content in the mixture such that the cellulose material is soluble in the inorganic molten salt hydrate media. Thus, it may be necessary to feed an inorganic molten salt hydrate medium with less water in case the lignocellulosic material has a significant water content. In another preferred embodiment, the water content of the lignocellulosic material is lowered before contact with the salt hydrate media.

A preferred inorganic molten salt hydrate medium has at least 40 wt % of $ZnCl_2$, more preferably 60 wt % of $ZnCl_2$, prior to the polysaccharide addition. The preferred salt content in salt hydrate medium is within the range of 60 to 85 wt %, not considering the biomass content. The salt content can be increased to compensate non-dried lignocellulosic material with high water content. A salt content higher than 85 wt % in the $ZnCl_2$ media is not preferred, as the salt content may exceed the saturation concentration, which leads to precipitation of $ZnCl_2$ from the salt media.

Although 70 wt % $ZnCl_2$ is the preferred inorganic molten salt hydrate, other inorganic molten salt hydrates may be used, alone or in combination with $ZnCl_2$, such as other zinc halides (bromide, iodide), or halides of other metals known to dissolve or swell cellulose, such as $CaCl_2$ and $LiCl$.

At least one transition metal salt may be present in the inorganic molten salt hydrate to enhance dehydration in the sugar alcohol dehydration step. Preferable metal salts are transition metal halides, preferably chlorides. Useful transition metal salts are the chlorides of the groups of Cu, Ni, Co, Fe, Mn, Cr, V and Ti. Preferred additional metal salts are $CuCl_2$ and $NiCl_2$.

In an alternate embodiment the dehydration step is carried out in the substantial absence of a transition metal salt. For example, the dehydration step may be carried out in an inorganic molten salt medium containing substantially one inorganic cation.

The ratio of inorganic molten salt hydrate media to polysaccharide or biomass is preferably from 1 to 50 wt/wt, more preferably from 5 to 20 wt/wt.

The inorganic molten salt hydrate temperature prior to contact with the lignocellulosic material may be higher than the desired temperature in the hydrolysis step. Or the mixture of lignocellulosic biomass and inorganic molten salt hydrate may be heated after mixing. Means of heat transfer known in the art can be utilized for obtaining the conditions required for the several modes of the present invention. The desired temperature is the one optimal for hydrolysis. In the hydrolysis step, addition of a mineral acid is desired, as shown in the following examples. Any of a number of mineral acids can be used, such as hydrochloric acid, hydrofluoric, sulfuric, phosphoric, and the like. Hydrochloric acid is the preferred acid, as it can be easily removed from the molten salt hydrate media by flash distillation, or stripping with nitrogen, or other suitable means known in the art.

Preferably the acid molality (mol acid per 1000 g of inorganic molten salt hydrate and acid mixture) is higher than 0.2 molal and lower than 2 molal, more preferably from 0.4 to 0.8 molal. Higher concentrations of acid than 2 molal may promote glucose degradation to undesirable compounds.

In an alternate embodiment the hydrolysis reaction is carried out in the substantial absence of a mineral acid. The advantage of this embodiment is that no subsequent removal of mineral acid is necessary. In this embodiment the hydrolysis reaction requires a reaction temperature of 85° C. or higher.

The hydrolysis temperature is such as to obtain a high hydrolysis rate, but a low degradation of glucose to undesired compounds. In practice, preferred temperatures are higher than 70° C. (85° C. if no acid catalyst is present), and lower than 150° C., more preferably higher than 90° C. and lower than 120° C. To ensure the desired temperature in the hydrolysis step, added gases, preferably oxygen-free gases, may be added to the reaction system as heat transfer media. The hydrolysis time, or residence time in the apparatus where the lignocellulosic material and molten salt hydrate and mineral acid are contacted, is such as to obtain full hydrolysis of polysaccharides, such as cellulose and hemicellulose, if present. In practice, the residence time should be from 10 to 180 minutes, preferably from 30 to 60 minutes.

Equipments to effect the hydrolysis can be batch reactors, continuous stirred tank reactors (CSTR) or a sequence of 2 or more CSTRs, continuous tubular reactors, fluidized bed reactors (suspended biomass particles whose cellulose is being dissolved), screw reactors, rotating reactors with or without ball milling or any suitable means of contacting the phases. In the case of batch reactors, several parallel reactors can be used, so the subsequent homogeneous phase process steps can be kept continuous. The whole process sequence can also be done in a batch way, but the continuous process is preferred. Advantages of a continuous process over a batch process are well known to one skilled in the art.

The dissolution and hydrolysis convert the hydrolyzable polysaccharide material (cellulose and/or hemicellulose or starch) to C6 (and C5) monosaccharides (hexitols and pentitols sugars). After the hydrolysis step the lignin can be fully separated from the inorganic molten salt hydrate and sugar solution. Suitable means to separate the insoluble lignin from the molten salt hydrate and sugar solution are filtration, centrifugation, decantation, use of hydrocyclones, settling, gas flotation, addition of an organic phase to which lignin would preferably interface, or a combination of these methods. A preferred method is centrifugation or the use of hydrocyclones, with and additional filtration to prevent any solid from being sent to further catalytic hydrogenation. Lignin is preferably further washed to remove salt still present in the solid cake, prior to further use.

Lignin can be used as a heat source to the process, and as a way of producing hydrogen to be used in the subsequent process steps. Hydrogen can be generated by any suitable process known in the art, such as lignin pyrolysis, steam reforming, or electrolysis of water from electricity produced by burning lignin.

In a preferred embodiment of the invention process, acid (if present) is removed prior to hydrogenation. As illustrated in the examples, acids have an inhibiting effect on the hydrogenation of glucose to sorbitol. In prior art hydrolysis processes, separation of volatile acids such as hydrochloric acid is difficult, as it forms an azeotrope with water. Fortunately, the azeotrope is broken in inorganic molten salt hydrate solutions, such as the $ZnCl_2$ concentrated solution preferred in the process of the present invention, as a result of which hydrochloric acid can be easily separated by flashing, distillation, countercurrent or concurrent stripping.

Hydrolysis is carried out at a temperature sufficient to provide a significant gas phase fugacity of hydrochloric acid. Other non-volatile acids such as sulfuric or phosphoric acid can be removed by chemical treatment, preferably forming insoluble compounds.

Due to the additional chemical consumption cost of non-volatile acids, the volatile hydrochloric acid is the preferred acid for use herein. Hydrochloric acid can be removed in the same step as lignin removal, for example if flotation is used for lignin removal (with nitrogen or air, preferably nitrogen, acting as stripping gas and flotation agent).

Hydrochloric acid can also be removed in the same step as hydrogenation, for example by effecting a countercurrent hydrogenation, where hydrogen is fed to the bottom of the reactor and the mixture of hydrochloric acid, glucose and molten salt hydrate is fed previously to the catalyst bed region—in this case a previous mass contact region with suitable mass contact devices can also exist. Hydrochloric acid is removed together with hydrogen at the top of the reactor. The hydrogen/hydrochloric acid mixture may be bubbled through water for hydrochloric acid removal. Suitable countercurrent contacting devices upstream from the reaction zone can be bubble cap trays, Raschig rings, structured packings, or a combination of contact and reaction structures, such as internally finned monoliths (IFM).

Hydrogenation temperature is such as to obtain a high hydrogenation rate but low degradation of glucose to undesired compounds. In practice, preferred temperatures are higher than 70° C. and lower than 150° C., more preferably higher than 90° C. and lower than 120° C. In practice it is preferred to work with pressures higher than 10 bar, preferably higher than 30 bar, more preferably higher than 50 bar, and temperatures lower than 120° C. Pressures higher than 200 bar are not economically advantageous.

The hydrogenation may be carried out at a LHSV of 0.05 to 5 h-1 and a molar excess of hydrogen with respect to the sugars (monosaccharides) being reduced of at least 2, preferably at least 3-fold.

Reaction is effected by contacting the molten salt hydrate and sugar solution with a catalyst. A preferred means for contact is a fixed bed catalyst. Alternative ways of contact are slurry reactors, expanded bed, moving beds—which can make it easier to replenish catalyst (and activity) continuously or intermittently. The preferred reactor is a trickle bed (or flooded bed) reactor, as the high catalyst holdup and the employed conditions do not result in significant catalyst deactivation.

Alternatively, when catalyst deactivation is significant, parallel reactors can be used, or the catalyst may be changed or regenerated as needed. Ways of heat removal in the reaction known in the art can also be employed. In practice, the inorganic molten salt hydrate can adsorb a significant part of the heat released during glucose hydrogenation, when the inorganic molten salt hydrate to biomass ratios of the invention are used. Additional procedures, such as product recycle, high gas/feed ratio can also be employed to minimize the heat increase due to glucose hydrogenation.

Suitable hydrogenation catalysts are the catalysts well known in sugar hydrogenation, such as Ru/C, Raney Ni or Raney Cu, Ni supported on carbon or alumina. Preferably the active catalyst component is selected from the noble metals of the series Ru, Rh, Pd and Pt, or a transition metal of the series Cu, Cr, Co, Ni, Fe. The preferred catalyst is Ru/C, as it is known to be less prone to leaching. Suitable support materials include activated carbon, aluminum oxide, hydrotalcites, silicates, titanates, zirconates, and other metallic oxides such as $SnO_2$, $Bi_2O_5$, $Sb_2O_5$, $MoO_3$, $WO_3$, mixed oxides such as $SiO_2$—$Al_2O_3$, $SiO_2$—$TiO_2$, $Al_2O_3$—$ZnO$, $SiO_2$—$ZrO_2$, $SiO_2$—$SnO_2$, $SiO_2$— $MoO_3$, $SIO_2$—$WO_3$, metallic salts such as $AlPO_4$, $FePO_4$, $Zn_3(PO_4)_2$, $Mg_3(PO_4)_2$, $Ti_3(PO_4)_4$, $Zr_3(PO_4)_4$. Basic oxides can also be used, such as MgO, BeO, $La_2O_3$, $CeO_2$, $Pr_2O_3$, $Nd_2O_3$, $SmO_2$, $ZrO_2$. Homogeneous, non-supported catalysts can also be used, but they are usually not stable at the temperatures, preferably higher than 200° C., required for the dehydration step.

The desired reaction product is a product with at least 98 wt % of glucose or monosaccharide sugars present, available for conversion to sorbitol or the correspondent sugar alcohols. C6 sugars are hydrogenated to hexitols and C5 sugars are hydrogenated to pentitols.

Another possible embodiment of the invention is a one-pot combination of hydrolysis and hydrogenation, as it is possible to hydrogenate glucose to sorbitol even in the presence of the acid necessary for hydrolysis. In such a case it may be necessary to remove the lignin prior to contact of the lignocellulosic material with the molten salt hydrate, the acid and the hydrogenation catalyst (as it is difficult to separate the solid catalyst from the solid lignin). Lignin removal by just dissolving the lignocellulosic material without effecting concomitant hydrolysis is not practical due to the high viscosity of the solution of unconverted cellulose in the hydrated molten salts.

After hydrogenation of glucose to sorbitol, or other monosaccharides to the correspondent sugar alcohols, dehydration is performed to produce the desired isosorbide or correspondent (di)anhydro sugar alcohol. One or two dehydrations are possible from the starting sugar alcohol, to first form an anhydro sugar alcohol and finally a dianhydro sugar alcohol.

The inorganic molten salt hydrate and sugar alcohols solution is sent to an additional reactor to effect the dehydration of sugar alcohols (sorbitol) to isosorbide or the correspondent anhydro sugar alcohols. Temperatures from 160 to 320° C. can be used, preferably from 220 to 280° C. Pressures of 0.1 to 10 MPa are suitable, preferably from 2 to 6 MPa. Preferably hydrogen atmosphere is employed, as it advantageously increases the yield of isosorbide. Additional conditions are LHSV from 0.1 to 5 h-1.

Preferably the product of the hydrogenation step—inorganic molten salt hydrate and sugar alcohols solution and remaining hydrogen are sent to the dehydration reactor. Conventional methods can be used to increase the temperature to the desired temperature range. Methods such as heat exchange with reaction product, furnaces, heating devices in the reactor, tube reactor, addition of a hot recycle flow and the like can be used, as long as the disclosed pressure, temperature, residence time (LHSV) are used. Full conversion of sorbitol is attained in the disclosed conditions.

Preferably a transition metal salt is used together with the inorganic molten salt hydrate and sorbitol or polyol solutions. The molar ratio of additional salt cation to polyol is from 0.01 to 5, preferably 0.1 to 1.0, more preferably 0.2 to 0.5. The combination of the inorganic molten salt hydrate media and the additional transition metal salt results in increased selectivity and conversion. It is also believed that the presence of hydrogen during the dehydration step further enhances the dehydration activity and selectivity. It is possible to form some amount of reduced metal during this step. Such metals can be separated by filtration and can be converted again to salt by contact with acid. In any event, the preferred additional salts, pressure and temperature are such that the formation of reduced metals is minimized.

After the dehydration, the resulting isosorbide or equivalent anhydro sugar alcohols can be separated from the molten salt hydrate media by known separation techniques. A preferred separation technique is extraction with hydrocarbons at temperatures higher than 100° C., where the solubility of isosorbide is significant. The hydrocarbons are then cooled and the isosorbide or equivalent anhydro sugar alcohols are recovered by precipitation. A preferred hydrocarbon to effect the separation is xylene. Another preferred separation technique involves the vaporization of isosorbide, which has a vapor pressure significantly higher than sorbitol or anhydrosorbitol.

Stripping with water vapor or air at low pressure and high temperature can be used. In this case it is necessary to work at a temperature higher than the melting temperature of the (molten) salt, as water will also be removed. For $ZnCl_2$ the melting point is 275° C.

After stripping of the desired compounds water can be re-added to the inorganic molten salt hydrate media. It is also possible to use an additional salt such as KCl in the hydrated inorganic molten salt to lower the melting point of anhydrous molten salt $ZnCl_2$.

One water molecule is consumed in the hydrolysis of each glucosidic moiety to form glucose when the glucosidic bond is broken, but two water molecules are generated in sorbitol dehydration, so there is a need to continuously remove water from the molten salt hydrate, in order to continuously maintain the desired molten salt hydrate composition. This can be effected by heating and stripping the hydrated molten salt with inert gas or oxygen to remove the required amount of water. This can be effected in combination with the removal of isosorbide, for example, when it is removed by vaporization of the compound, or during a regeneration step of the inorganic molten salt hydrate, if necessary.

The pentitols (originating from the hydrolysis of hemicellulose) dehydration yields just monoanhydrides, which are more difficult to separate, and thus it is preferred to effect first a hemicellulose removal, prior to contacting the cellulose feedstock with the inorganic molten salt hydrate media.

In an alternate embodiment the dianhydro sugars and/or anhydro sugars are derivatized in the inorganic molten salt hydrate medium. The purpose of this derivatization is to render the (di)anhydro sugars less polar, and hence less soluble in the inorganic molten salt hydrate medium. In general, this is achieved by removing or blocking free hydroxyl moieties in the (di)anhydro sugar molecule.

One example of a suitable derivation reaction is a further dehydration of the (di)anhydro sugar molecule.

Another example is reacting the hydroxyl moieties with a suitable reactant, such as a dialkyl carbonate, an alcohol, or a carboxylic acid. Examples of suitable dialkyl carbonates include dimethyl carbonate and diethyl carbonate. Examples of suitable carboxylic acids include formic acid, acetic acid, and acetic anhydride. It will be understood that acetic anhydride is, strictly speaking, not a carboxylic acid. In the present context it is considered equivalent to a carboxylic acid, as its reaction results in the formation of ester moieties in the (di) anhydro sugar molecule.

Particularly preferred is etherification with an alcohol, such as methanol or ethanol. Dimethyl isosorbide and diethyl isosorbide are examples of compounds obtained by the etherification reaction. The derivatization may also produce a mixture of mono- and di-ethers.

Etherification with longer chain alcohols, in particular fatty alcohols having an alkyl chain comprising from about 8 to about 30 carbon atoms, preferably from about 12 to about 20 carbon atoms, produces compounds that can be used as plasticizers in polymeric materials.

Esterification with longer chain carboxylic acids, in particular fatty acids having an alkyl chain comprising from about 8 to about 30 carbon atoms, preferably from about 12 to about 20 carbon atoms, produces compounds that can be used as plasticizers in polymeric materials.

The anhydro sugars may be polymerized with dicarboxylic acids to form biodegradable polyesters. An example of a suitable dicarboxylic acid is terephtalic acid.

The resulting compounds are poorly soluble in the inorganic molten salt hydrate medium, allowing them to be readily separated from the medium. The derivatized compounds are useful as fuel additives and/or fuel substitutes. Dimethyl isosorbide and diethyl isosorbide have a high cetane value, making them particularly suitable as additives in diesel fuel. Due to their oxygen content they contribute to a clean burning of the diesel fuel.

It may also be necessary to remove non-converted soluble compounds, oligomers and carbonaceous material from the inorganic molten salt hydrate, or even monoanhydrides. This may be the case during a regeneration step. One of the ways of effecting such regeneration comprises dilution in water to make oligomers insoluble, followed by water removal. Another way of effecting such a regeneration is similar to the processes used to regenerate $ZnCl_2$ when used as a solvent in coal hydrocracking: oxidation of organic material by contact with air at higher temperatures—it may be necessary to add HCl in the burning cycle to prevent the formation of ZnO, and replenish removed water later.

The hydrated inorganic molten salt, after separation, is recycled to the beginning of the process. To make the continuous nature of the disclosure more apparent, the process steps of the preferred mode of the invention are described hereafter, making reference to FIG. 1.

Figure 1:
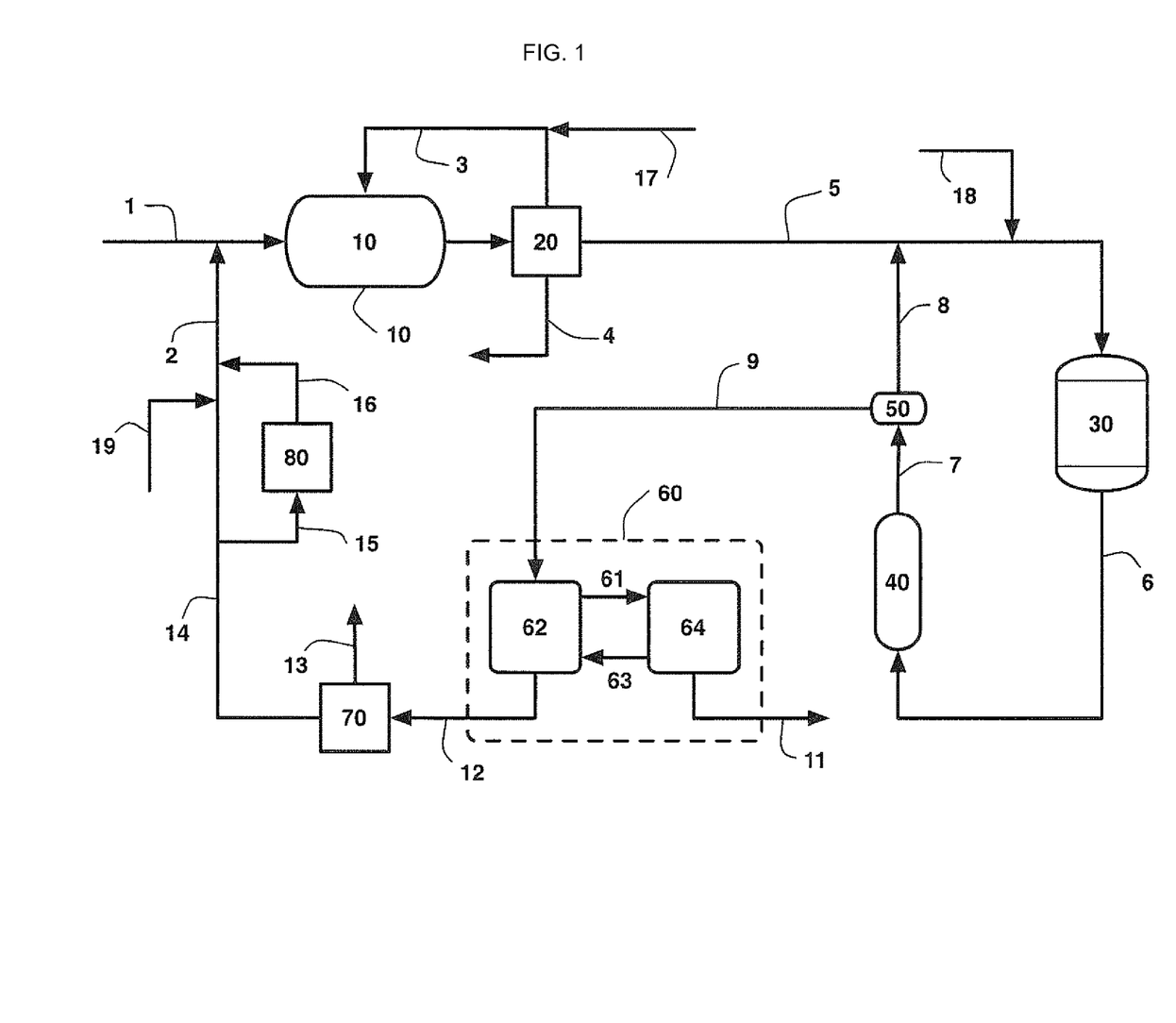
FIG. 1 is a scheme of a preferred embodiment of the process comprising the combined steps of dissolution and hydrolysis of cellulose, hydrogenation of glucose to sorbitol and dehydration to isosorbide in molten salt hydrate medium.

Line 1 represents the flux of lignocellulosic biomass material. Consider in the preferred embodiment of the disclosure that it has been separated from the hemicellulose first. The lignocellulosic material (1) is mixed with the inorganic molten salt hydrate mixture (2) and sent together or separately to the reactor (10) to effect dissolution and, together with hydrochloric acid (3), effect the hydrolysis.

The mixture of inorganic molten salt hydrate, glucose and acid are discharged from the hydrolysis reactor, and sent to the separation (20) of lignin (4), used elsewhere in the process, and removal of hydrochloric acid (3) to be recycled to the hydrolysis step. A small make-up of hydrochloric acid may be necessary (17) to compensate for losses.

The mixture of inorganic molten salt hydrate and glucose (5) is mixed with recycle hydrogen (8) and make-up hydrogen (18) and sent to the hydrogenation reactor (30). In the hydrogenation reactor (30) glucose is converted to sorbitol. Steps of heat transfer and heat recovery to the reactor feed and from the reactor product are not shown, but are obvious to those skilled in the art.

The mixture of inorganic molten salt hydrate and sorbitol (6) is sent to the dehydration reactor (40), where at proper higher temperature conditions sorbitol is converted to isosorbide. The mixture of inorganic molten salt hydrate, isosorbide and hydrogen (7) is sent to a separator. Steps of heat transfer and heat recovery to the reactor feed and from the reactor product are not shown, but are well known to those skilled in the art. Recovered hydrogen (8) is separated from the inorganic molten salt hydrate and isosorbide mixture (9) in separator (50). Inorganic molten salt hydrate and isosorbide mixture (9) are sent to a separation step (60), where isosorbide and anhydro sugar alcohols (11) are separated from the hydrated molten salt mixture (12).

Although other ways can be used to separate isosorbide from the inorganic molten salt hydrate, the procedure disclosed in (60) involves contacting the inorganic molten salt hydrate and isosorbide mixture (9) with xylene or a similar hydrocarbon in a suitable contact device (62) at a temperature higher than 120° C. The apolar hydrocarbon/sorbitol phase (61) is separated and sent to a contact device at a low temperature (64).

The isosorbide crystals precipitate at temperatures lower than 60° C. The temperatures, pressures, contacting times and number of contact stages at (62) and (64), together with flow of (61) and (63) can be selected such that all the isosorbide is removed from the inorganic molten salt hydrate.

There is water consumption in the hydrolysis (10), but 2 water molecules are generated in sorbitol dehydration at (40), so there is a need to continuously remove water from the inorganic molten salt hydrate at (70), resulting in a recovered water flow (13), in order to continuously maintain the desired inorganic molten salt hydrate composition (14).

A regeneration of part of the inorganic molten salt hydrate might be useful, being effected at (80), from a fraction of the inorganic molten salt hydrate main flow (15), resulting in a regenerated inorganic molten salt hydrate (16), returning again to the main inorganic molten salt hydrate recycle (2). A small make-up (19) of inorganic molten salt hydrate may be necessary, from salt lost and recovered from lignin burning, for example. The inorganic molten salt hydrate in the desired composition (2) is then continuously added to the lignocellulosic material (1), resulting in a fully continuous process.

It will be apparent to those skilled in the art that variations in the process scheme are possible without departing from the scope of invention.

Other claimed variation of the invention process is the processing of particular biomasses that produce saccharose such as sugarcane or sugar beet. In this case saccharose would be first separated from the biomass and could be combined with biomass after hemicellulose removal and subjected to hydrolysis. The saccharose will hydrolyze to glucose and fructose. Glucose and fructose are further hydrogenated to a mixture of sorbitol and mannitol. Double dehydration of sorbitol and mannitol yields respectively isosorbide and isomannide (dianhydromannitol or 1,4:3,6-dianhydro-D-mannitol). Isomannide can be further separated the same way as the isosorbide.

Without wishing to limit the claims of the present invention to a mechanism of improved production of isosorbide from cellulose material, it is believed that the dissolution of cellulose and full hydrolysis is possible thanks to:

(a) interaction of the hydrated inorganic molten salt ions with the hydroxyl groups, resulting in a dissolved material, accessible to acid hydrolysis;

(b) the hydrated inorganic molten salt media (including the additional transition metal salt) being an electron acceptor—strongly interacting with the hydroxyl groups, weakening the C—O bond, and allowing intramolecular nucleophilic substitution, and thus catalyzing the internal dehydration of sorbitol molecules to the first and the second dehydration (isosorbide) products;

(c) the presence of hydrogen is believed to favor the formation of +1 charged cations in the inorganic molten salt hydrate media which have significant polarity and electron acceptor capabilities;

(d) the dehydration takes place in the absence of added acids, and thus degradation and tarring is not favored;

(e) the sorbitol molecule conformation, due to interaction of hydroxyls with the inorganic molten salt hydrate cations, favors the 1,4 and 3,6 dehydration in the sorbitol over 1, 5 or 2,5;

(f) the sorbitol dilution by effect of inorganic molten salt hydrate also makes the oligomerization products unfavorable;

In order to illustrate the application of the present invention, the use of inorganic molten salt hydrate media to effect the sequential dissolution, hydrolysis, hydrogenation and dehydration of cellulose material, the effect of the inorganic molten salt hydrate is set forth by the results of the Examples and Figures described hereafter.

Further interpretations of the nature and the mechanism of the increased yield of isosorbide or analogous dehydrated polyols do not alter the novelty of the present invention which will be now illustrated by the following Examples, which should not be considered as limiting the claims.

EXAMPLES

Example 1

Effect of Inorganic Molten Salt Hydrate on Cellulose Dissolution—Comparison with Cellulose Stability in Other Solvents Cellulose, long fibers, was mixed in different solvents to form a 5 wt % content mixture and immediately sent to an optical microscopy controlled heating cell. After the heating step, solutions were heated from 25° C. up to 130° C. at 5° C./minute and kept in this condition for 10 minutes.

Table 1 shows the observed results.

TABLE 1

| Solvent | Aspect |
| --- | --- |
| $ZnCl_2$, 70%, in water | Full dissolution in 8 minutes after temperature reached 65° C. |
| BMIM Cl (1-butyl-3-methylimidazolium chloride | No change |

An organic ionic liquid solvent known to dissolve cellulose made no change in the material in the same time frame, even after 10 minutes at 130° C. On the other hand the dissolution of cellulose in $ZnCl_2$ is fast and complete. The example shows that dissolution was complete in a small time frame.

Example 2

Effect of Different Salt Concentrations in Cellulose Hydrolysis

Figure 2:
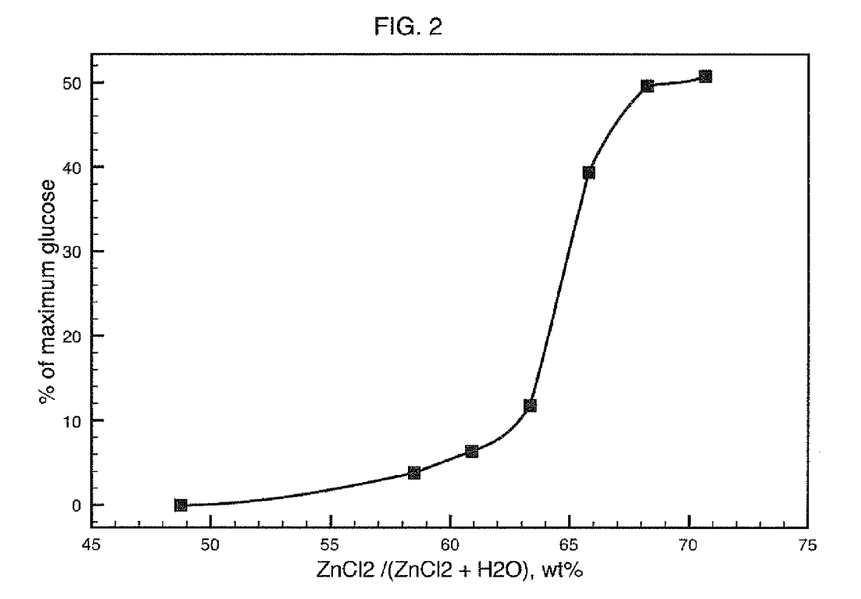
FIG. 2 is a graph illustrating the effect of increasing the salt concentration in the $ZnCl_2$ molten salt hydrate media on the hydrolysis of cellulose, according to Example 2.

In a stirred reactor, 0.5 g of cellulose was added to 6.0 g of salt solutions with different concentrations. Concentrated hydrochloric acid was added to each of the solutions to result in 0.4 molal of HCl. Hydrolysis time was 30 minutes at a temperature of 100° C. FIG. 2 shows the HPLC results referenced to maximum glucose yield. It can be seen that at salt concentrations lower than 50 wt % no glucose was produced. Increasing the salt content increased the hydrolysis, and above 67 wt % the further increase was small.

Without intending to limit the scope of the invention by any explanation, it is believed that a concentration of salt of at least 65 wt % is necessary to ensure a fast and complete dissolution. At higher salt concentrations, no additional gain was obtained.

Example 3

Effect of Time on the Hydrolysis

Figure 3:
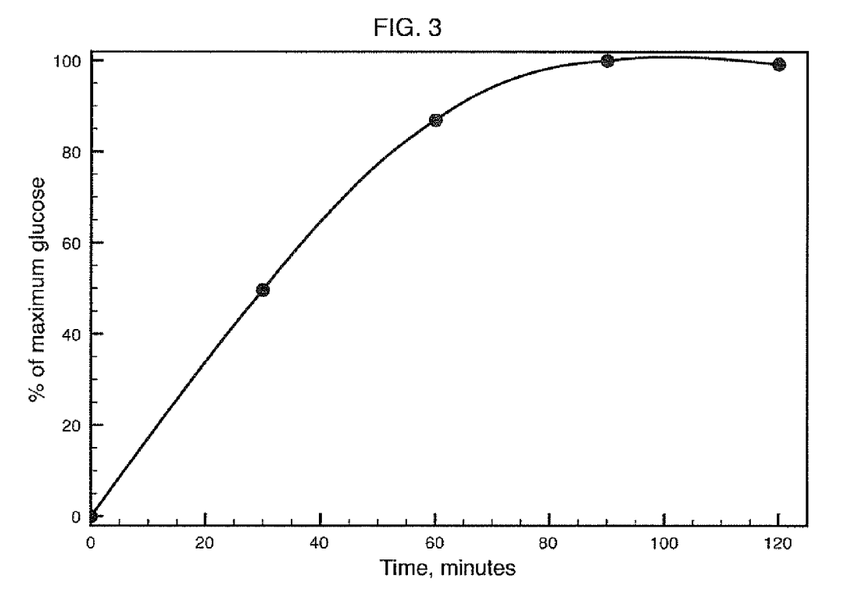
FIG. 3 is a graph illustrating the effect of time on the hydrolysis of cellulose in a $ZnCl_2$ 70 wt % molten salt hydrate media, according to Example 3.

In a stirred reactor, 0.5 g of cellulose was added to 6.0 g of salt solution with 70 wt % of $ZnCl_2$, and hydrochloric acid content of 0.4 molal, with a temperature of 100° C. The reaction was repeated four different times. The results are shown in FIG. 3. It can be seen that it is possible to completely hydrolyze the cellulose to glucose by the present invention, resulting in a solution of sugar and inorganic molten salt hydrate. Sugar oligomer peaks detected in HPLC also disappeared at 90 minutes. Small amounts of probably decomposition products were formed at longer times.

Example 4

Hydrolysis in Inorganic Molten Salt Media of Lignocellulosic Biomass

Ball milled pine wood samples (0.5 g) were mixed with 6.0 g of salt solution with 70 wt % of $ZnCl_2$ and hydrochloric acid content of 0.4 molal. The reaction was effected for 30, 60 and 90 minutes. The product was ultracentrifuged and full separation of a black/violet material, lignin, at the top, and a clear salt/sugar solution at the bottom. When salt solutions were dissolved in 10 times the water weight, some cellulose precipitated in the 30 minute product, and no precipitation took place in the 60 and 90 minutes products. At 30 minutes glucose oligomers, glucose and C5 and lower sugar peaks were observed in HPLC. At 60 and 90 minutes the same HPLC peak areas were obtained, higher than in 30 minutes and no oligomers could be seen, meaning full hydrolysis had taken place.

The results show that in the first hydrolysis step of invention process it is possible to obtain from real biomass the full conversion of cellulose and hemicellulose to the corresponding monosaccharide sugars and separation of lignin from the sugars.

Example 5

Effect of Acid Content on Hydrolysis

Figure 4:
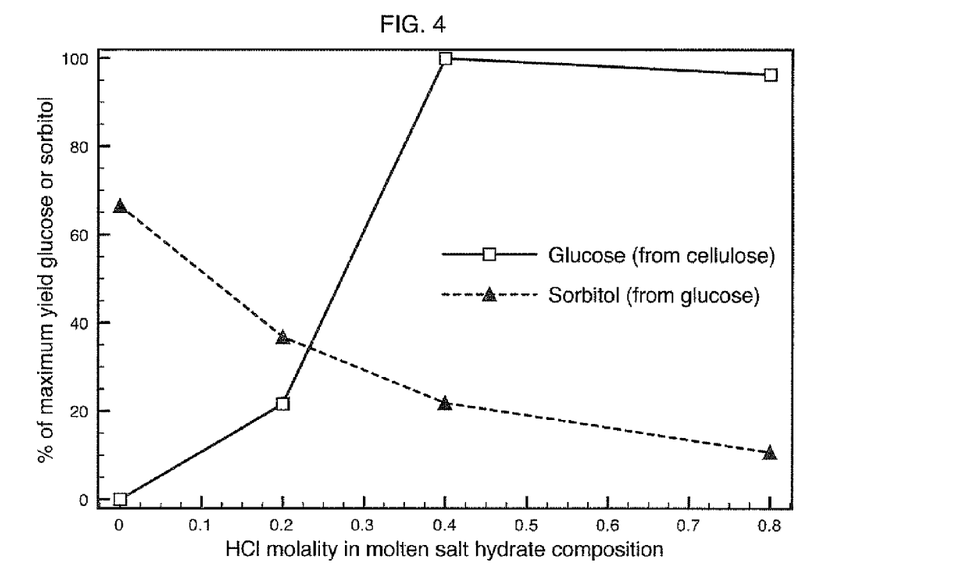
FIG. 4 is a graph illustrating the effect of hydrochloric acid on the hydrolysis of cellulose to glucose, according to Example 5, and on the hydrogenation of glucose to sorbitol, according to Example 6

Cellulose (0.5 g) and 6.0 g of hydrated inorganic molten salt solutions of 70 wt % $ZnCl_2$ of different hydrochloric acid contents (zero, 0.2, 0.4 and 0.8 molal) were mixed and subjected to hydrolysis for 1 h at 100° C. Results are presented in FIG. 4.

It can be seen that without additional acid no hydrolysis is effected, just dissolution takes place. Molality of just 0.2 molal is insufficient but above 0.4 full hydrolysis at these conditions takes place.

Example 6

Effect of Acid Content on Glucose Hydrogenation in the Hydrated Inorganic Molten Salt Media of Invention Glucose (0.5 g) with 0.25 g of Ru/C catalyst and 6.0 g of hydrated inorganic molten salt solutions of 70 wt % $ZnCl_2$ of different hydrochloric acid contents (no acid, 0.2, 0.4 and 0.8 molal) were mixed and subjected to hydrogenation at 50 bar for 1 h at 100° C. Results are presented in FIG. 4. It can be seen that the additional acid inhibits the hydrogenation of glucose to sorbitol. According to the invention, it is preferred to remove the acid before the hydrogenation step of the present embodiment.

Example 7

Figure 5:
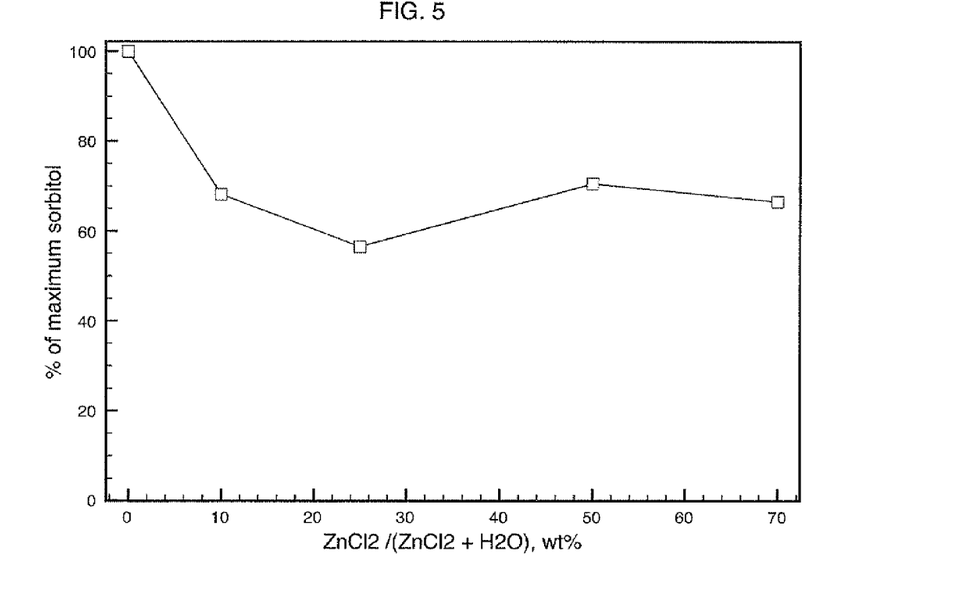
FIG. 5 is a graph that illustrates the effect of increasing the salt concentration in the $ZnCl_2$ molten salt hydrate media on the hydrogenation of glucose to sorbitol, according to Example 6.

Effect of Hydrated Inorganic Molten Salt Concentration on the Hydrogenation Step of Sugar to Polyol of Invention Glucose sugar (0.5 g) with 0.25 g of Ru/C catalyst and 6.0 g of hydrated inorganic molten salt solutions of different $ZnCl_2$ content and no hydrochloric acid were mixed and subjected to hydrogenation at 50 bar for 1 h at 100° C. Results of conversion to sorbitol are presented in FIG. 5.

Without $ZnCl_2$, hydrogenation was faster, apparently being completed in 30 minutes, as there was no further change in reactor pressure profile after this time. Further addition of $ZnCl_2$ inhibited the reaction, but small concentrations of $ZnCl_2$ (10 wt %) inhibited the reaction in the same way as the higher concentration solutions (70 wt %).

According to the invention, it is possible to effect the hydrogenation of glucose to sorbitol in hydrated inorganic molten salt and glucose mixtures, although in a less efficient way (needing to be compensated with a higher LHSV-time and/or catalyst).

Besides the inhibiting effect of the salt, there is no gain in diluting the solution prior to hydrogenation or trying to remove the salt partially.

Example 8

Catalytic Sorbitol Hydrogenolysis at Higher Temperature in Hydrated Inorganic Molten Salt Sorbitol (0.5 g) with 0.25 g of Ru/C catalyst was mixed with 6.0 g of water or hydrated inorganic molten salt solutions of varying $ZnCl_2$ concentrations at 220° C., 50 bar and 1 h reaction time. With water, significant conversion to hydrogenolysis (isomerization and the production of lower molar weight polyols) products is evidenced. As the salt content is increased, hydrogenolysis is severely inhibited, and at 70 wt % $ZnCl_2$ inorganic molten salt medium, small amounts of just 2 products remain: anhydroglucitols, products of dehydration of sorbitol, having one (sorbitans) or two (isosorbide) fewer water molecules. The results show that the hydrated inorganic molten salt media inhibit the hydrogenolysis products and favor the formation of dehydration products, under hydrogenation conditions.

Example 9

Process of Dehydration of Sorbitol in Hydrated Inorganic Molten Salt Media and Effect of Additional Salts and Comparison with Dehydration in Aqueous Media in Hydrogen and Nitrogen Atmosphere Sorbitol (0.5 g) was mixed with 6.0 g of $ZnCl_2$ 70 wt % or water. $CuCl_2$ was added in some tests as an additional salt, in a quantity of 1 mol per 2 mol of sorbitol. Temperature of reaction was 250° C. for 1 h reaction time, and pressure 50 bar of $H_2$ or $N_2$. HPLC results showed just 3 peaks, assigned to sorbitol, anhydrosorbitols (sorbitans) and isosorbide (1,4:3, 6-dianhydrosorbitol).

Results of HPLC normalized are presented on TABLE 2.

TABLE 2

| Test | medium | additional salt | atmosphere | Sorbitol mol % | Sorbitan mol % | Isosorbide mol % |
|---|---|---|---|---|---|---|
| 1 | water | Cu 1:2 Sorbitol | Hydrogen | 6.5 | 48.52 | 44.97 |
| 2 | $ZnCl_2$ 70 wt % | none | Hydrogen | 2.5 | 25.26 | 72.25 |
| 3 | $ZnCl_2$ 70 wt % | Cu 1:2 Sorbitol | Hydrogen | 0.6 | 4.47 | 94.93 |
| 4 | water | Cu 1:2 Sorbitol | Nitrogen | 24.44 | 9.39 | 66.16 |
| 5 | $ZnCl_2$ 70 wt % | none | Nitrogen | 12.4 | 47.53 | 40.06 |
| 6 | $ZnCl_2$ 70 wt % | Cu 1:2 Sorbitol | Nitrogen | 1.74 | 13.85 | 84.41 |

The hydrated inorganic molten salt is able to effect the dehydration of sorbitol—and surprisingly to a higher extent in hydrogen atmosphere instead of nitrogen atmosphere. It can be seen that the addition of additional $CuCl_2$ salt increased the dehydration activity. The best results were obtained with the additional salt dissolved in $ZnCl_2$ hydrated inorganic molten salt in hydrogen atmosphere of the present invention.

Example 10

Invention Process of Sorbitol Dehydration in Different Hydrated Inorganic Molten Salt Medium and Several Additional Salts Sorbitol (0.5 g) was mixed with 6.0 g of different salts ($ZnCl_2$ 70 wt % or $CaCl_2$ 42.7 wt % or LiCl 45.4 wt %) and additional salts in a cation/sorbitol ratio of 0.1. Reaction pressure was 50 bar of hydrogen atmosphere and temperature of 230° C. for 1 h time.

Results of sorbitol conversion for each salt media and additional salts are presented in TABLE 3.

TABLE 3

| Sorbitol conversion | $ZnCl_2$ | $CaCl_2$ | LiCl |
|---|---|---|---|
| $RuCl_3$ 1:10 | 21.9 | 11.7 | 7.7 |
| $CoCl_2$ 1:10 | 42.4 | 0.1 | 1.3 |
| $CuCl_2$ 1:10 | 88.7 | 7.6 | 7.4 |
| $NbCl_5$ 1:10 | 64.7 | 13.5 | 5 |
| $NiCl_2$ 1:10 | 84.2 | 5.6 | 8 |

It can be seen that $CuCl_2$ and $NiCl_2$ are the most active salts. Conversion of sorbitol was significant just in $ZnCl_2$ hydrated inorganic molten salt media. $CaCl_2$ and LiCl hydrated inorganic molten salt media were not effective for sorbitol conversion, even though these salts were reported in the prior art as superior to $ZnCl_2$ in the hydrated inorganic molten salt hydrolysis of cellulose. A salt known to be more easily reduced, like $RuCl_3$, to RuO, did not show a high sorbitol conversion, so formation of in situ HCl is not the main mechanism of sorbitol conversion by dehydration of the present invention.

Example 11

Effect Time on Dehydration in Inorganic Molten Salt Hydrate

Inorganic molten salt hydrate of $ZnCl_2$ 70 wt % (6.0 g) was mixed with 0.5 g of sorbitol and a mass equivalent of 1 mol of $CuCl_2$ per 2 mol of sorbitol. Reaction temperature was 235° C. and pressure 50 bar. The products analysis results for several reaction times are presented in FIG. 6.

Figure 6:
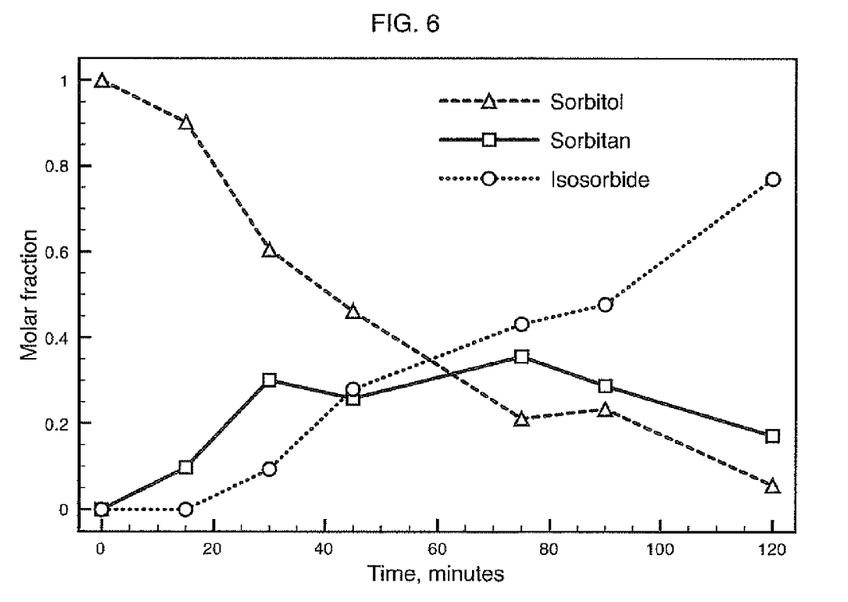
FIG. 6 is a graph that illustrates the effect of reaction time on the dehydration of sorbitol in the $ZnCl_2$ molten salt hydrate media in the presence of Copper chloride, according to Example 11.

The Figure shows the following product profiles, with sorbitol being dehydrated to the first dehydration product (sorbitan), followed by further dehydration of sorbitans to isosorbide. The main products of first dehydration are 1,4 and 3,6 anhydrosorbitol, and not 2, 5 or 1,5 anhydro products—which further dehydration does not proceed according to the art.

Example 12

Figure 7:
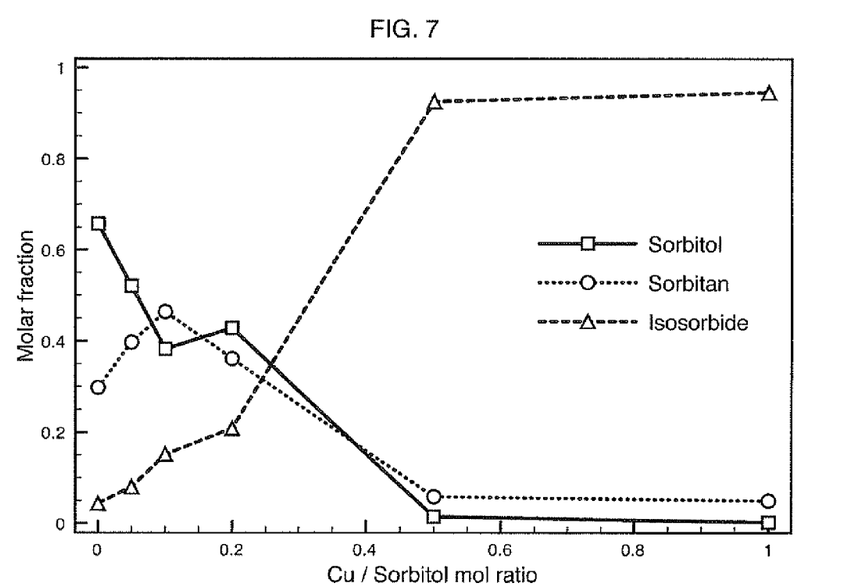
FIG. 7 is a graph that illustrates the effect of different concentrations of additional salt ($CuCl_2$) on the dehydration of sorbitol in the $ZnCl_2$ molten salt hydrate media, according to Example 12.

Effect of Additional Salt Content on Dehydration in Inorganic Molten Salt Hydrate Inorganic molten salt hydrate of $ZnCl_2$ 70 wt % (6.0 g) was mixed with 0.5 g of sorbitol and different contents of $CuCl_2$ (from zero to 1 mol of Cu per mol of sorbitol). Reaction time was 1 h, temperature of 235° C. and pressure of 50 bar. The results are shown in FIG. 7.

It can be seen that increased content of an additional salt resulted in increased dehydration activity. Main gain in dehydration activity happened in 0.5 mol of Cu/mol of sorbitol in the feed. It was possible to completely convert the sorbitol and produce mostly isosorbide in 1 h reaction time at 235° C.

LIST OF REFERENCES

[1] WERPY, T.; PETERSEN, G.; ADEN, A.; BOZELL, J.; HOLLADAY, J.; WHITE, J. MANHEIM, A. Top value added chemicals from biomass. Vol. I: Results of screening for potential candidates from sugars and synthesis gas. USA DOE (Department of Energy) Report, 2004.
[2] HEINZE, T.; LIEBERT, T., Unconventional methods in cellulose functionalization, PROGRESS IN POLYMER SCIENCE 26 (9) (2001) 1689-1762.
[3] EL SEOUD, O. A.; HEINZE, T., Organic esters of cellulose: New perspectives for old polymers. Advances in Polymer Science, vol. 186, (2005), p. 103-149.
[4] LEHMANN, C. G. Physiological Chemistry, vol. I, Blanchard & Lea, Philadelphia, 1855, p. 267 ("Moreover, chloride of zinc converts cellulose first into a matter which is colored blue by iodine, then into sugar, and lastly into a humus-like substance").
[5] N. J. CAO, Q. XU, L. F. CHEN, Acid-hydrolysis of cellulose in zinc-chloride solution, APPLIED BIOCHEMISTRY AND BIOTECHNOLOGY 51-2 (1995) 21-28.
[6] P. L. RAGG, P. R. FIELDS, The development of a process for the hydrolysis of lignocellulosic waste, PHILOSOPHICAL TRANSACTIONS OF THE ROYAL SOCIETY OF LONDON SERIES A-MATHEMATICAL PHYSICAL AND ENGINEERING SCIENCES 321 (1561) (1987) 537-547.
[7] FLÈCHE, G.; HUCHETTE, M., Isosorbide—preparation, properties and chemistry. Starch/Stärke, vol. 38, n 1, (1986), S 26-30.
[8] STOSS, P.; HEMMER, R., 1,4:3,6-dianhydrohexytols. Advances in Carbohydrate Chemistry and Biochemistry, vol. 49 (1991), p. 93-173.
[9] BOCK, K.; PEDERSEN, C.; THOGERSEN, H. Acid catalyzed dehydration of alditols. Part 1-D-glucitol and D-mannitol. Acta Chemica Scandinavica B, vol. 35 (1981), p. 441-449.
[10] MONTASSIER, C.; DUMAS, J. M.; GRANGER, P.; BARBIER, J. Deactivation of supported copper based catalysts during polyol conversion in aqueous phase. Applied Catalysis A: General, vol. 121 (1995), p. 231-244.
[11] MONTASSIER, C.; MÉNÉZO, J. C.; NAJA, J.; GRANGER, P.; BARBIER, J.; SARRAZIN, P.; DIDILLON, B. Polyol conversion into furanic derivatives on bimetallic catalysts; nature of the catalytic sites. Journal of Molecular Catalysis, vol. 91 (1994), p. 119-128

MONTASSIER, MÉNÉZO, J. C.; NAJA, J.; BARBIER, J.; DOMINGUEZ, J. M.; SARRAZIN, P.; DIDILLON, B. Preparation and characterization of copper based bimetallic catalysts. Journal of Molecular Catalysis, vol. 91 (1994), p. 107-117
DUCLOS, A.; FAYET, C.; GELAS, J. A simple conversion of polyols into anhydroalditols. Synthesis, October 1994, p. 1087-1090.

What is claimed is:
1. A process for converting a polysaccharide-containing material to a fuel additive or a fuel substitute material, said process comprising the steps of:
 (i) dissolving the polysaccharide-containing material in an inorganic molten salt hydrate;
 (ii) hydrolyzing components of the cellulose-containing material in the inorganic molten salt hydrate medium to form monosaccharides;
 (iii) hydrogenating the monosaccharides obtained in step (ii) in the inorganic molten salt medium to the corresponding sugar alcohols;
 (iv) dehydrating the sugar alcohols obtained in step (iii) in the inorganic molten salt medium to form the corresponding anhydro sugars and/or dianhydro sugars;
 (v) derivatizing the (di)anhydro sugars obtained in step (iv), in the inorganic molten salt medium, to form derivatized (di)anhydro sugars having reduced solubility in the inorganic molten salt hydrate medium.
2. The process of claim 1 wherein the polysaccharide-containing material comprises cellulose and/or lignocellulose.
3. The process of claim 2 wherein lignin is removed from the inorganic molten salt medium prior to step (ii).
4. The process of claim 1 wherein the polysaccharide-containing material comprises hemicellulose.
5. The process of claim 4 wherein hemicellulose is removed from the inorganic molten salt medium prior to step (ii).
6. The process of claim 1 wherein step (ii) is conducted in the substantial absence of hemicellulose.
7. The process of claim 1 wherein step (ii) is carried out in the presence of an acidic catalyst.
8. The process of claim 7 wherein the acidic catalyst is a mineral acid.
9. The process of claim 8 wherein the mineral acid is hydrochloric acid.
10. The process of claim 1 wherein step (ii) is carried out in the substantial absence of a mineral acid.
11. The process of claim 1 wherein the inorganic molten salt hydrate comprises $ZnCl_2$, $CaCl_2$, LiCl, or a mixture thereof.
12. The process of claim 1 wherein the monosaccharides comprise glucose.
13. The process of claim 12 wherein the monosaccharides consist essentially of glucose.
14. The process of claim 1 wherein step (iii) is carried out in the presence of a hydrogenation catalyst.
15. The process of claim 14 wherein the hydrogenation catalyst comprises a noble transition metal.
16. The process of claim 15 wherein the hydrogenation catalyst comprises Ruthenium.
17. The process of claim 15 wherein the hydrogenation catalyst comprises activated carbon as a carrier.
18. The process of claim 1 wherein the sugar alcohols comprise sorbitol.
19. The process of claim 18 wherein the sugar alcohols consist substantially of sorbitol.

20. The process of claim 11 wherein the inorganic molten salt medium comprises at least 60 wt. % $ZnCl_2$.

21. The process of claim 1 wherein, in step (iv), the selectivity to the formation of dianhydro sugars is at least 80%.

22. The process of claim 1 wherein the dianhydro sugars comprise isosorbide.

23. The process of claim 22 wherein the dianhydro sugars consist substantially of isosorbide.

24. The process of claim 1 wherein the inorganic molten salt medium comprises substantially one inorganic salt.

25. The process of claim 24 wherein the substantially one inorganic salt is $ZnCl_2$.

26. The process of claim 1 wherein the derivatization comprises etherification or esterification.

27. The process of claim 26 wherein the derivatization is etherification.

28. The process of claim 1 wherein the derivatized dianhydro sugars comprise dimethyl isosorbide and/or diethyl isosorbide.

29. The process of claim 1 wherein the derivatization comprises polymerization with a dicarboxylic acid.

30. The process of claim 29 wherein the dicarboxylic acid is terephtalic acid.

31. The process of claim 28 wherein the derivatized dianhydro sugars consist substantially of dimethyl isosorbide.

32. The process of claim 26 wherein etherification is carried out with a fatty alcohol.

33. The process of claim 26 wherein esterification is carried out with a fatty acid.

* * * * *